US00PP22891P2

(12) United States Plant Patent
Dümmen

(10) Patent No.: US PP22,891 P2
(45) Date of Patent: Jul. 24, 2012

(54) *CALIBRACHOA* PLANT NAMED 'DUEALGO'

(50) Latin Name: ***Calibrachoa* sp.**
Varietal Denomination: Duealgo

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 8 days.

(21) Appl. No.: 12/928,570

(22) Filed: Dec. 14, 2010

(51) Int. Cl.
*A01H 5/00* (2006.01)

(52) U.S. Cl. ..... Plt./413

(58) Field of Classification Search ..... Plt./413
See application file for complete search history.

*Primary Examiner* — Susan McCormick Ewoldt
(74) *Attorney, Agent, or Firm* — C. A. Whealy

(57) ABSTRACT

A new and distinct cultivar of *Calibrachoa* plant named 'Duealgo', characterized by its compact, outwardly spreading to trailing and decumbent plant habit; freely branching growth habit; early flowering habit; numerous large yellow orange-colored flowers with red-colored centers and venation; and good garden performance.

1 Drawing Sheet

Botanical designation: *Calibrachoa* sp.
Cultivar denomination: 'DUEALGO'.

BACKGROUND OF THE INVENTION

The present invention relates to a new and distinct cultivar of *Calibrachoa* plant, botanically known as *Calibrachoa* sp. and hereinafter referred to by the name 'Duealgo'.

The new *Calibrachoa* plant is a product of a planned breeding program conducted by the Inventor in Rheinberg, Germany. The objective of the breeding program is to create new uniform *Calibrachoa* plants with large attractive flowers.

The new *Calibrachoa* plant originated from a cross-pollination made by the Inventor in July, 2008 in Rheinberg, Germany of a proprietary selection of *Calibrachoa* sp. identified as code number A05-5410-003, not patented, as the female, or seed, parent with a proprietary selection of *Calibrachoa* sp. identified as code number F-0318-2375, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2010.

Asexual reproduction of the new *Calibrachoa* plant by vegetative terminal cuttings in a controlled greenhouse environment in Rheinberg, Germany since May, 2010 has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'Duealgo'. These characteristics in combination distinguish 'Duealgo' as a new and distinct *Calibrachoa* plant:

1. Compact, outwardly spreading to trailing and decumbent plant habit.
2. Freely branching growth habit.
3. Early flowering habit.
4. Numerous large yellow orange-colored flowers with red-colored centers and venation.
5. Good garden performance.

The new *Calibrachoa* can be compared to plants of the female parent selection. Plants of the new *Calibrachoa* differ primarily from plants of the female parent selection in flower color as plants of the female parent selection have orange-colored flowers.

The new *Calibrachoa* can be compared to plants of the male parent selection. Plants of the new *Calibrachoa* differ primarily from plants of the male parent selection in flower size as plants of the new *Calibrachoa* have larger flowers than plants of the male parent selection.

Plants of the new *Calibrachoa* can be compared to plants of *Calibrachoa* 'KLECA016120', disclosed in U.S. Plant Pat. No. 19,488. In side-by-side comparisons, plants of the new *Calibrachoa* differed primarily from plants of 'KLECA016120' in the following characteristics:

1. Plants of the new *Calibrachoa* were more compact than plants of 'KLECA016120'.
2. Plants of the new *Calibrachoa* had thicker stems than plants of 'KLECA016120'.
3. Plants of the new *Calibrachoa* had larger and darker green-colored leaves than plants of 'KLECA016120'.
4. Plants of the new *Calibrachoa* had larger flowers than plants of 'KLECA016120'.
5. Plants of the new *Calibrachoa* and 'KLECA016120' differed slightly in flower color.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph is a top perspective view of a typical flowering branch of 'Duealgo'.

DETAILED BOTANICAL DESCRIPTION

The aforementioned photograph and following observations, measurements and values describe plants grown during the summer in 10.5-cm containers in a glass-covered greenhouse in Rheinberg, Germany under commercial *Calibrachoa* production practices. During the production of the plants, day and night temperatures averaged 18° C. and light levels averaged 4,500 lux. Rooted young plants were pinched one time three weeks after planting and were 13 weeks old when the photograph and description were taken. In the following description, color references are made to The Royal Horticultural Society Colour Chart, 1995 Edition, except where general terms of ordinary dictionary significance are used.

Botanical classification: *Calibrachoa* sp. 'Duealgo'.

Parentage:

- *Female, or seed, parent*.—Proprietary selection of *Calibrachoa* sp. identified as code number A05-5410-003, not patented.
- *Male, or pollen, parent*.—Proprietary selection of *Calibrachoa* sp. identified as code number F-0318-2375, not patented.

Propagation:

- *Type*.—By vegetative cuttings.
- *Time to initiate roots, summer*.—About five days at 20° C.
- *Time to initiate roots, winter*.—About seven days at 20° C.
- *Time to produce a rooted young plant, summer*.—About three weeks at temperatures of 20° C.
- *Time to produce a rooted young plant, winter*.—About four weeks at temperatures of 20° C.
- *Root description*.—Fine, fibrous; white in color.
- *Rooting habit*.—Freely branching; dense.

Plant description:

- *Plant and growth habit*.—Compact, outwardly spreading to trailing and decumbent plant habit; freely branching habit with about 10 to 15 lateral branches; pinching enhances branching; vigorous growth habit.
- *Plant height*.—About 13 cm.
- *Plant diameter*.—About 30 cm.

Lateral branch description:

- *Length*.—About 20 cm.
- *Diameter*.—About 3 mm.
- *Internode length*.—About 2.9 cm.
- *Strength*.—Strong.
- *Aspect*.—Initially upright to outwardly spreading to trailing and decumbent.
- *Texture*.—Pubescent.
- *Color*.—Close to 146C.

Foliage description:

- *Arrangement*.—Before flowering, alternate, simple; after flowering, opposite, simple.
- *Length*.—About 2.3 cm.
- *Width*.—About 7.8 mm.
- *Shape*.—Oblanceolate.
- *Apex*.—Rounded.
- *Base*.—Cuneate.
- *Margin*.—Entire.
- *Texture, upper and lower surfaces*.—Pubescent.
- *Venation pattern*.—Pinnate; arcuate.
- *Color*.—Developing and fully expanded leaves, upper surface: Close to 137A; venation, close to 144B. Developing and fully expanded leaves, lower surface: Close to 137C; venation, close to 144B.
- *Petiole*.—Length: About 2 mm. Diameter: About 1 mm. Texture, upper and lower surfaces: Pubescent. Color, upper and lower surfaces: Close to 144B.

Flower description:

- *Flower arrangement and habit*.—Single salverform flowers arising from leaf axils; freely flowering habit with usually about 30 open flowers and flower buds per plant; flowers face upright or outwardly.
- *Fragrance*.—None detected.
- *Natural flowering season*.—Early flowering habit, plants of the new *Calibrachoa* initiate and develop flowers about four to five weeks after planting; plants flower continuously from the spring until the autumn in Germany.
- *Flower longevity*.—Individual flowers last about seven to ten days on the plant; flowers not persistent.
- *Flower diameter*.—About 3 cm.
- *Flower length* (*height*).—About 3.4 cm.
- *Flower throat diameter*.—About 1 cm.
- *Flower tube length*.—About 1.8 cm.
- *Flower tube diameter, base*.—About 2 mm.
- *Flower bud*.—Shape: Elongated oblong. Length: About 2.2 cm. Diameter: About 4 mm. Color: Close to 59A.
- *Corolla*.—Arrangement: Five petals fused at the base and opening into a flared trumpet. Petal length from throat: About 1.3 cm. Petal lobe width: About 1.2 cm. Petal shape: Roughly spatulate. Petal apex: Rounded and shallowly cordate. Petal margin: Entire. Petal texture, upper and lower surfaces: Smooth, glabrous. Throat texture: Smooth, glabrous. Tube texture: Smooth, glabrous. Color: Petal, when opening, upper and lower surfaces: Close to 22B. Petal, fully opened, upper surface: Close to 21B; venation, close to 46A; color becoming closer to 11A with development. Petal, fully opened, lower surface: Close to 21D; venation, close to 187A. Throat: Close to 17C; venation, close to 187A. Tube: Close to 151D; venation, close to 187A.
- *Calyx*.—Arrangement: Star-shaped calyx with five sepals; sepals fused at the base. Sepal length: About 1.2 cm. Sepal width: About 2.7 mm. Sepal shape: Lanceolate. Sepal apex: Acute. Sepal margin: Entire. Sepal texture, upper and lower surfaces: Pubescent. Color, upper surface: Close to 137C. Color, lower surface: Close to 137D.
- *Peduncles*.—Length: About 1.9 cm. Diameter: About 2 mm. Angle: About 45° from stem axis. Strength: Moderately strong. Texture: Pubescent. Color: Close to 143C.
- *Reproductive organs*.—Stamens: Quantity/arrangement: Six per flower. Filament length: About 1 cm. Filament color: Close to 150C. Anther shape: Ellipsoidal. Anther length: About 1 mm. Anther color: Close to 14A. Pollen amount: Scarce. Pollen color: Close to 14A. Pistils: Quantity: One per flower. Pistil length: About 1 cm. Style length: About 9 mm. Style color: Close to 144C. Stigma shape: Ellipsoidal. Stigma color: Close to 144A. Ovary color: Close to 144C.

*Seed/fruit*.—Seed and fruit development have not been observed on plants of the new *Calibrachoa*.

Garden performance: Plants of the new *Calibrachoa* have been observed to have good garden performance and tolerate wind, rain and temperatures ranging from about 5° C. to about 40° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'Duealgo' as illustrated and described.

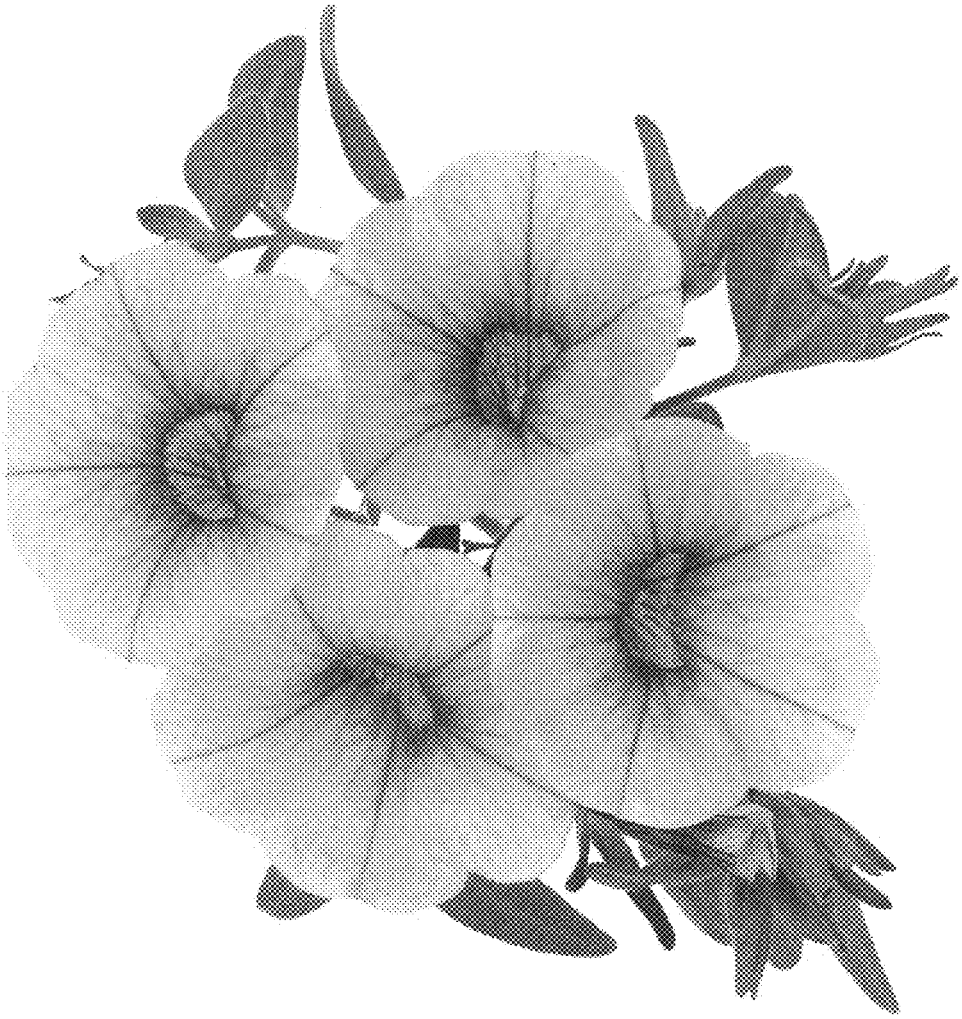

* * * * *